United States Patent [19]

D'Addezio

[11] Patent Number: 4,938,514
[45] Date of Patent: Jul. 3, 1990

[54] PORTABLE HAND TOOL FOR HOLDING A NEEDLE CAP WHILE INSERTING A SYRINGE NEEDLE INTO THE CAP

[76] Inventor: Sandra A. D'Addezio, 6082 University Ave., Saginaw, Mich. 48604

[21] Appl. No.: 280,342

[22] Filed: Dec. 6, 1988

[51] Int. Cl.⁵ .................. A61M 5/32; B25B 9/00
[52] U.S. Cl. .................. 294/16; 24/507; 24/510; 128/919; 294/28; 294/99.2; 604/192
[58] Field of Search .............. 294/3, 8.5, 11, 16, 294/28–31.1, 32, 33, 99.2, 104, 106, 118; 24/500, 507, 509, 510; 81/3.44, 13, 44; 128/346, 917, 919, DIG. 6; 206/365, 366; 604/192, 198, 263

[56] References Cited

U.S. PATENT DOCUMENTS

| | | | |
|---|---|---|---|
| 1,176,604 | 3/1916 | Sanders | 294/99.2 X |
| 1,259,458 | 3/1918 | Norris | 24/510 X |
| 1,608,498 | 11/1926 | Fisher | 294/118 |
| 2,316,731 | 4/1943 | Walter | 294/118 X |
| 2,593,054 | 4/1952 | Reagan et al. | 24/510 X |
| 2,618,499 | 11/1952 | Scharf | 294/28 |
| 3,559,515 | 2/1971 | Kyser | 294/99.2 X |
| 3,817,126 | 6/1974 | Koebbeman | 81/3.44 |
| 4,079,765 | 3/1978 | Hatayan | 81/44 |
| 4,226,459 | 10/1980 | Natalicio | 294/33 X |
| 4,596,562 | 6/1986 | Vernon | 604/192 |

FOREIGN PATENT DOCUMENTS 1019609  2/1966  United Kingdom .................. 294/28

Primary Examiner—Johnny D. Cherry
Attorney, Agent, or Firm—Learman & McCulloch

[57] ABSTRACT

A portable hand tool, for holding an elongate needle cap so that a syringe needle can safely be inserted into the cap, has a lever structure comprising a pair of juxtaposed, mating, pivotally connected levers. The levers at their front ends have marginal edges defining a cap receiving opening parallel to the axis of pivot. The structure provides a wall functioning as a base for the opening and a spring normally biases the front ends of the levers to a closed cap gripping position. The levers are operated by squeezing their rear ends to achieve a cap receiving and releasing position.

1 Claim, 1 Drawing Sheet

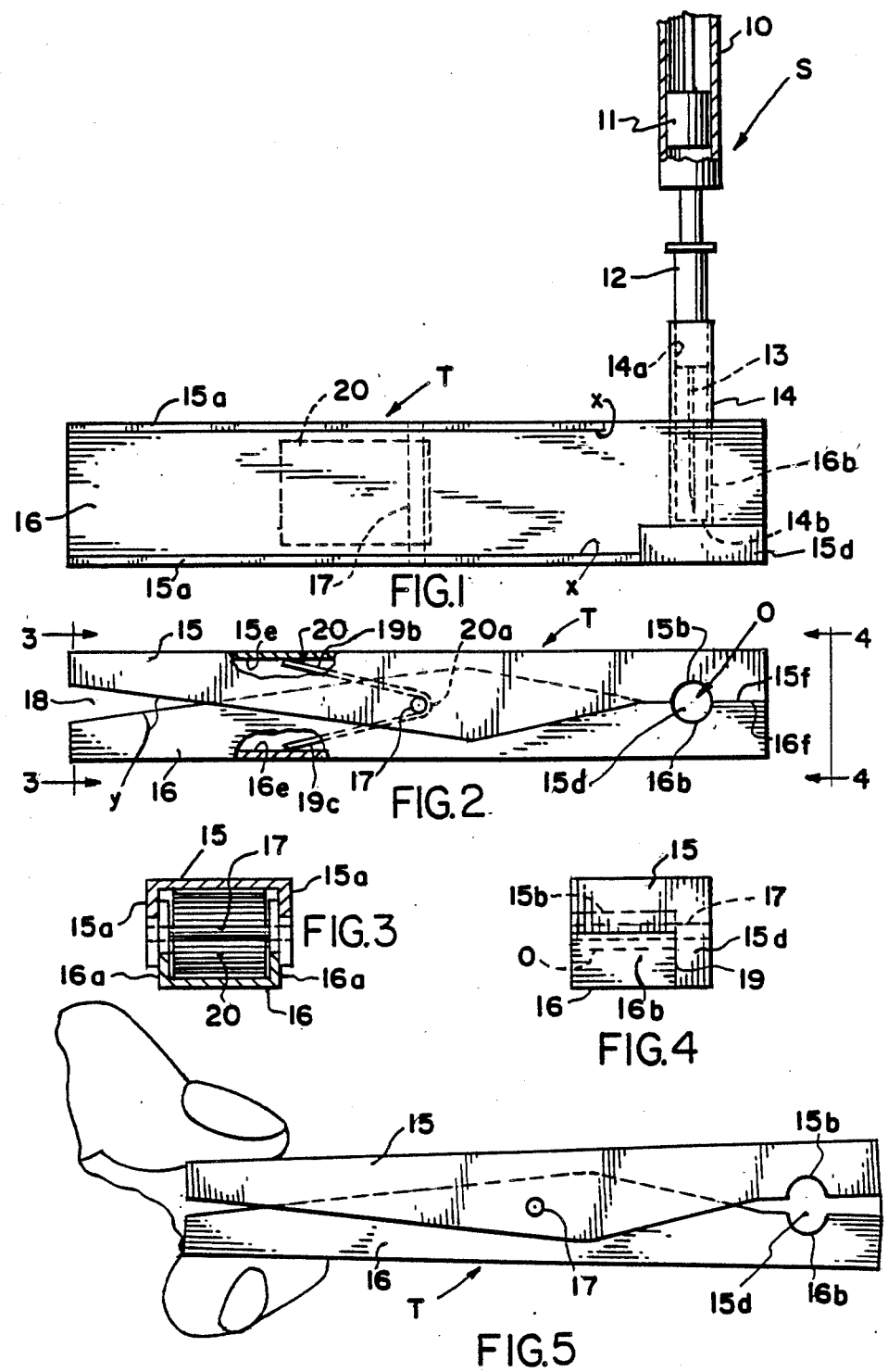

4,938,514

PORTABLE HAND TOOL FOR HOLDING A NEEDLE CAP WHILE INSERTING A SYRINGE NEEDLE INTO THE CAP

BACKGROUND OF THE INVENTION

This invention relates to the disposing of used syringe needles in hospitals, physician offices and medical laboratories and more particularly to a safety tool of a portable nature which is particularly useful in recapping a syringe needle, and which is also useful for uncapping it in the first place. Hypodermic syringes, when uncapped, have relatively fine diameter needles which are extremely sharp, so that even the most casual contact with the skin results in penetration. With the danger today of transmitting very debilitating and fatal diseases in this manner, used syringes need to be handled with great care. However, when syringes are handled routinely in work settings, even when the utmost care is exercised, it is inevitable that accidental penetration of the skin will occur when the user is holding the needle cap in one hand and seeking to insert the needle of the syringe into the cap with the other A number of devices have been previously proposed in connection with this problem as follows:

| | |
| --- | --- |
| 4,485,918 Mayer | 4,636,201 Ambrose et al |
| 4,573,975 Frist et al | 4,659,330 Nelson et al |
| 4,596,562 Vernon | 4,664,259 Landis |
| 4,623,336 Pedicano et al | 4,717,386 Simmons |

The foregoing prior suggestions have not, to my knowledge, met with particular success for a variety of reasons which the present invention obviates.

SUMMARY OF THE INVENTION

The present invention is characterized as a portable hand-held tool of simple and economic character which the user can readily move from place to place so that it will be available at any needle recapping site. The tool is elongate in nature and is manipulatable from an end which is remote from a cap clamping end so that the hand of the user holding the tool is never proximate the cap clamping end and the needle, as it is being inserted into the cap following use.

It is an object of the present invention to provide an improved hand tool, which, with safety considerations paramount, is designed to clamp and release a needle cap via the remote manipulation of the tool, so that, even if the person recapping the needle misses the cap when attempting reinsertion, there is no likelihood that the needle will accidentally penetrate the hands of the person using it.

Another object of the invention is to provide a reusable tool which promotes the safe disposal of a contaminated needle, and eliminates the danger to health presented by ordinary needle recapping operations.

A further object of the invention is to provide an elongate tool, manipulatable from one end to readily open and close a remote cap or sheath clamping opening which has a closed safety base for receiving the base of the needle cap, and which also facilitates the positioning of the cap in the tool.

Other objects and advantages of the invention will be pointed out specifically, or will become apparent from the following description, when it is considered in conjunction with the appended claims and the accompanying drawings.

IN THE DRAWINGS

FIG. 1 is a side elevational view showing a needle cap clamped in the tool, and a syringe needle as having been inserted in the cap;

FIG. 2 is a top plan view of the tool only, with portions broken away in the interest of clarity to better illustrate the clamp spring;

FIG. 3 is a transverse sectional elevational view taken on the line 3—3 of FIG. 2;

FIG. 4 is an end elevational view taken on the line 4—4 of FIG. 2; and

FIG. 5 is a top plan view showing the fingers of the user manipulating one end of the device to open the cap receiving opening in the opposite remote end of the device.

DETAILED DESCRIPTION

Referring now more particularly in the first instance to FIG. 1, I have schematically illustrated a typical disposable syringe, generally designated S, which has the usual cylindrical tubular container 10 with a movable plunger 11, and an extending needle support 12 for a hypodermic needle 13. The needle 13 is, of course, hollow and has communication with the lower end of tubular body 10. A plastic sheath or cap 14, which is gripped by the novel and improved tool T of the present invention, has an open upper end with a tapered marginal wall 14a receiving the needle mount portion 12 of the syringe in a detachable, press-fit relationship. Normally, the cap or sheath 14 is frictionally held on the lower end of needle mount 12. The cap 14 is of cylindrical configuration and has a closed bottom end 14b.

Referring now more particularly to FIGS. 2 through 5, the tool T of the present invention is shown as comprised of a pair of side by side levers, generally designated 15 and 16, which are pivotably connected by a pin 17. At their rear ends, levers 15 and 16 are channel-shaped and the lever 16 is received within the lever 15, lever 16 being cut away as at x to accommodate this. The levers 15 and 16, respectively, have side walls 15a and 16a in lapped relationship so that pin 17 can extend through openings which are provided in the side walls 15a and 16a to mount the pin 17. It is to be noted that walls 15a and 16a taper and gradually reduce as at y, as they proceed in a rearward direction, to leave the opening 18 between them at their rear ends.

The front end of each of levers 15 and 16 is provided with a semicircular mating recess, 15b and 16b, respectively, to form a composite opening O, which, when the tool is in the closed position shown in FIG. 2, is of the size and configuration to receive and tightly clamp the needle cap 14. Cut in the lower end of lever 16, is a recess 19 for receiving a laterally protruding bottom lip or wall 15d provided on lever 15. The opening O then extends to a predetermined depth, such that base 14b of the needle cap 14 bottoms on the marginal base wall 15d provided on the lever 15.

In FIGS. 1 through 4, the levers 15 and 16 are shown as biased to an opening closing position in which the vertical abutment surfaces 15f and 16f are in relatively tight engagement. This engagement is maintained by the enclosed leaf spring, generally designated 20, which includes a loop portion 20a encircling pin 17, and a pair of legs 19b and 19c which, respectively, engage the connecting web walls 15e and 16e of levers 15 and 16, and force the levers 15 and 16 to the FIG. 2 position.

THE OPERATION

In operation, when a user's fingers press the rear ends of levers 15 and 16 and squeeze them together, the space 18 is reduced, as the levers 15 and 16 pivot about pin 17, and opening O is enlarged as the recessed portions 15b and 16b separate This operation, from the remote rear ends of levers 15 and 16, opens the tool for reception of the empty cap 14 which is placed in position then in the opening O. The syringe which has been used can then be replaced in the cap 14, once the levers 15 and 16 are restored to normal position by the spring 19 to tightly clamp the cap 14 in the position in which it is shown in FIG. 1. As FIG. 1 indicates, the syringe S has been moved vertically down until the needle 13 is encapsulated within cap 14 and the needle mount 12 is frictionally engaged within the upper end of the cap 14. When the cap 14 is in inserted position, the base 14b has moved downwardly to engage the wall portion 15d which properly positions the cap 14 for the recapping operation.

There is no possibility of the needle going all the way through the plastic base 14b of the cap 14 and endangering the user, inasmuch as surface 15d prevents further travel of the needle. Even if the needle 13 should miss the cap 14, no harm is done because the user is grasping the rear ends of the levers 15 and 16.

Once the syringe S is in engaged position, as shown in FIG. 1, the tool user can simply invert the tool and, with the levers 15 and 16 again squeezed, release the cap 14 and syringe S to a waste container.

While one embodiment of the invention has been described in detail, it will be apparent to those skilled in the art that the disclosed embodiment may be modified. Therefore, the foregoing description in all aspects is to be considered exemplary rather than limiting in any way, and the true scope of the invention is that defined in the following claims.

What is claimed is:

1. A portable hand tool for use in holding an elongate needle receiving tubular cap, having a closed base end held by the tool and an exposed open end, so that a syringe needle can be safely inserted into the cap comprising:
   a. a pair of interfitting, elongate, longitudinally extending co-extensive levers having remote front and rear ends, one of the levers having side wall portions receiving the other lever, the said other lever having side wall portions which are lapped by the side wall portions of said one lever;
   b. the levers being configured to have confronting jaw portions at their front ends with abutting planar, longitudinal surfaces having mating, semi-cylindrical openings therein forming a socket with an axis for receiving said cap axially between said jaws, and rear ends which are spaced apart when the said jaw surfaces are in abutting relation; and
   c. laterally extending pivot structure connecting the lapped side wall portions of the levers interjacent said front and rear ends;
   d. spring means cooperable with said pivot structure to normally bias said jaw portions to a pivoted position in which the said jaw surfaces abut and a needle cap may be clamped in said socket;
   e. one of said jaw portions being cut away laterally perpendicularly to the axis of said socket to define a notch and the other jaw portion having a laterally extending protruding ledge extending into said notch perpendicularly to said socket to fully underlie said socket and prevent a needle from axially passing through the cap and tool and injuring someone.

* * * * *